(12) United States Patent
Berba et al.

(10) Patent No.: US 6,440,111 B1
(45) Date of Patent: Aug. 27, 2002

(54) ULTRATHIN FLUID MANAGEMENT ARTICLE

(75) Inventors: Maria Luisa Berba, Quezon (PH); Robert J. Graeme, Morrisvile; Andrew J. Hagerty, Doylestown, both of PA (US); Barbara A. Ludwig, Bedminster, NJ (US); Stella Yi Zhang, Shanghai (CN)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/406,036

(22) Filed: Sep. 27, 1999

(51) Int. Cl.$^7$ .................................................. A61F 13/15
(52) U.S. Cl. .................. 604/385.01; 604/381; 604/368
(58) Field of Search ................................ 604/358, 367, 604/385.23, 386, 387, 365, 374, 375, 384, 385.21, 381

(56) References Cited

U.S. PATENT DOCUMENTS

| | | | |
|---|---|---|---|
| 4,324,246 A | | 4/1982 | Mullane et al. ............. 128/287 |
| 4,463,045 A | * | 7/1984 | Ahr et al. .................... 428/131 |
| 4,589,876 A | | 5/1986 | Van Tilburg ............ 604/385 R |
| 4,657,538 A | * | 4/1987 | Becker et al. .............. 604/381 |
| RE32,649 E | | 4/1988 | Brandt et al. ............... 604/368 |
| 4,738,676 A | * | 4/1988 | Osborn, III ................. 604/385 |
| 4,950,264 A | | 8/1990 | Osborn, III ............. 604/385.1 |
| 5,009,653 A | * | 4/1991 | Osborn .................... 604/385.1 |
| 5,248,309 A | * | 9/1993 | Serbiak et al. .............. 604/368 |
| 5,575,786 A | | 11/1996 | Osborn, III ................. 604/387 |
| 5,591,149 A | * | 1/1997 | Cree et al. .................. 604/378 |
| 5,613,963 A | | 3/1997 | Boisse et al. ............... 604/384 |
| 5,704,929 A | * | 1/1998 | Bien ........................ 604/385.1 |
| 5,800,418 A | * | 9/1998 | Ahr et al. .................... 604/368 |
| 5,803,920 A | | 9/1998 | Gilman |
| 5,821,179 A | * | 10/1998 | Masaki et al. .............. 442/375 |
| 5,951,536 A | * | 9/1999 | Osborn, III et al. ........ 604/387 |
| 6,086,950 A | * | 7/2000 | Masaki et al. .............. 427/180 |
| 6,103,953 A | * | 8/2000 | Cree et al. ................... 604/365 |
| 6,107,539 A | * | 8/2000 | Palumbo et al. ............ 604/378 |
| H1909 H | * | 11/2000 | Ahr ............................. 156/296 |

FOREIGN PATENT DOCUMENTS

| | | |
|---|---|---|
| EP | 0 336 578 A | 10/1989 |
| EP | 0526225 A1 | 2/1993 |
| EP | 0 705 584 A | 4/1996 |
| EP | 0737462 A1 | 10/1996 |
| HU | 65807 | 7/1994 |
| WO | WO 95/17147 A1 | 6/1995 |

OTHER PUBLICATIONS

Hungarian Novelty Search Report for Application No. P 0003764 dated Feb. 12, 2001.

* cited by examiner

*Primary Examiner*—John G. Weiss
*Assistant Examiner*—Jacqueline Stephens

(57) ABSTRACT

The present invention relates to a fluid management article to be worn adjacent a user's perineum for collecting and/or absorbing low volumes of bodily fluids encountered both menstrually and intermenstrually. The article is particularly useful for everyday use, that is, for managing daily perspiration, vaginal discharge, post intercourse drainage, and other bodily fluids due to various conditions, such as infection.

24 Claims, 2 Drawing Sheets

US 6,440,111 B1

ULTRATHIN FLUID MANAGEMENT ARTICLE

FIELD OF THE INVENTION

The present invention relates to an extremely thin, fluid management article that is intended to be worn adjacent a user's perineum. The article is useful in collecting and/or absorbing low volumes of bodily fluids, such as menses, urine, and perspiration.

BACKGROUND OF THE INVENTION

Externally worn absorbent articles for managing discharged bodily fluids are well known in the art. A plethora of design features have evolved over the years in an effort to improve the performance of these articles, such as lateral extensions for wrapping around a user's undergarment, body-conforming means for diminishing any gaps between the article and the user's body, and the addition of highly absorbent and retentive materials, such as those materials commonly referred to as superabsorbents. An additional evolutionary aspect of these articles, is a reduction in article thickness (caliper).

The designers of the reduced caliper articles referred to above have maintained the absorptive capacity of the relatively thicker articles being replaced, thereby providing users with a thin and flexible article capable of managing significant volumes of fluid. For example Osborne, III, U.S. Pat. No. 4,950,264, discloses a thin and flexible sanitary napkin having a capacity great enough to handle medium to high menstrual flows. The napkins in '264 have a preferred caliper of less than about 2.6 millimeters and total fluid capacity of at least about 20.0 grams. Brandt et al., U.S. Pat. No. Re. 32,649, discloses absorbent articles comprising an intimate admixture of hydrophilic fiber material and hydrogel-forming particles, purportedly capable of holding high amounts of discharged body fluids.

More and more consumers are purchasing and wearing fluid management articles on an everyday basis, as compared to only during their menstrual period. Consumers may experience daily perspiration, vaginal discharge, post intercourse drainage, and other fluid discharges due to various conditions, such as infection. To manage the daily discharge and to feel "fresh", consumers must purchase and wear standard napkins or panty liners, dealing with the obtrusiveness and high absorptive capacity associated with these products. While articles such as those disclosed in '264 and '649 are suitable for managing significant volumes of fluid, they are overdesigned for managing low volumes, such as those encountered intermenstrually. Even the least absorbing articles commercially available in the U.S., such as CAREFREE panty liners and KOTEX LIGHTDAYS pantiliners, offer excess absorption capacity for light menstrual flow and intermenstrual discharge.

One approach to address managing low volumes of bodily fluids is disclosed in Boisse et al., U.S. Pat. No. 5,613,963. The article disclosed in '963 is a panty liner, consisting essential of a unitary sheet of nonwoven fabric constituting a primary liquid-retaining component and plurality of recesses on its top surface, and a liquid-impervious barrier layer. Boisse et al. teaches constructing the nonwoven fabric from a mixture of fiber types, with rayon fibers being a constant in the multitude of combinations. A disadvantage realized with this construction is that the rayon fibers are absorbent, and therefore may retain fluid at or near its skin-contacting surface. If the outer surface feels clammy to a user, then discomfort occurs, with an extreme case impelling the user to replace the article before its useful life has terminated.

What is still needed is a thin and flexible fluid management article that provides extreme comfort and adequate capacity for collecting and/or absorbing limited volumes of bodily fluid.

SUMMARY OF THE INVENTION

The present invention relates to a fluid management article to be worn adjacent a user's perineum for collecting and/or absorbing low volumes of bodily fluids encountered both menstrually and intermenstrually. The article is particularly useful for everyday use, that is, for managing daily perspiration, vaginal discharge, post intercourse drainage, and other bodily fluids due to various conditions, such as infection.

In accordance with one embodiment of the present invention, a fluid management article designed and configured to be worn adjacent a user's perineum, comprising an absorbent-free, liquid permeable structure having a first surface and a second surface opposite thereof; and a barrier layer covering at least a portion of the second surface, is provided. These articles being substantially free of absorbent material will collect fluid within the interstitial spaces (pores), to prevent fluid from transferring to unwanted surfaces.

In accordance with a second embodiment of the present invention, a fluid management article designed and configured to be worn adjacent a user's perineum, comprising a liquid permeable cover; a barrier layer; and an absorbent core intermediate the cover and the barrier layer; wherein the article has a total capacity of 1.2 grams or less, is provided.

In accordance with a third embodiment of the present invention, a fluid management article designed and configured to be worn adjacent a user's perineum, comprising a liquid permeable cover; a barrier layer; and an absorbent core intermediate the cover and the barrier layer; the absorbent core comprising 0.7 grams or less of absorbent material, is provided. Preferably, the absorbent material is substantially free of hydrogel-forming polymers.

DETAILED DESCRIPTION OF THE INVENTION

Figure 1:
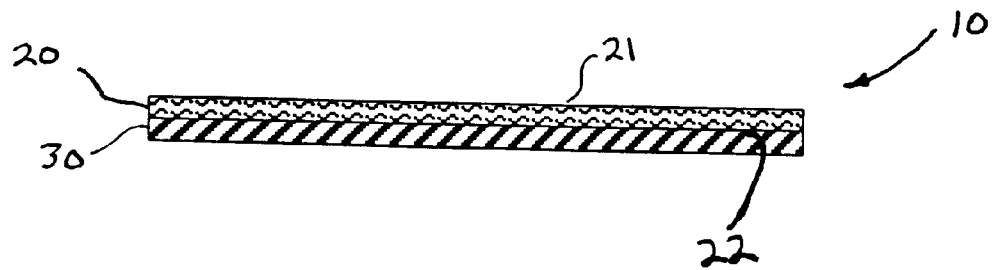
FIG. 1 is an end view of a fluid management article provided by the present invention having a liquid permeable structure and a barrier layer overlaying a garment-facing side of the structure.

The present invention relates to a fluid management article designed and configured to be worn adjacent a user's perineum, that is useful for collecting and/or absorbing low volumes of bodily fluids. Referring to FIG. 1, in a preferred embodiment, fluid management article 10 consists essentially of an absorbent-free, liquid permeable structure 20 having a first surface 21 to be worn facing the user's body and an opposing second surface 22 (garment-facing); and a barrier layer 30 covering at least a portion of the second surface 22. The liquid permeable structure 20 may exhibit the following, non-limiting configurations, a nonwoven web, a woven web, an apertured film, an apertured formed film, a substrate having flocked fibers thereon, a lamination of multiple layers of films or fibrous webs and combinations thereof, or the like. The absorbent-free, liquid permeable structure 20 is capable of collecting fluid within existing interstitial spaces (or pores), such as for example between non-absorbent fibers or within apertures/bosses. Any collected fluid will have a tendency to settle proximal the barrier layer 30, thereby minimizing fluid retention proximal the body-facing surface 21.

A liquid permeable structure in the form of flocked fibers may have a liquid permeable or impermeable carrier, such as a nonwoven web or a polymeric film. The carrier may comprise hydrophilic fibers, hydrophobic fibers, or combinations thereof. Methods of flocking onto a substrate are known in the art of fabric manufacture. See for example, U.S. Pat. Nos. 3,436,442 and 3,679,929. In addition, European Pat. App. No. 737,462 discloses an absorbent article having flocked fibers on its external surface.

Examples of apertured films and apertured formed films useful as the liquid permeable structure are disclosed in the following U.S. Pat. Nos. 4,710,186 and 4,342,314.

Nonwoven webs are preferred as the absorbent-free, liquid permeable structure 20. Suitable fibers useful for making such nonwoven webs include polyolefin and polyester fibers. A polypropylene nonwoven web is particularly suitable for the liquid permeable structure 20, wherein the polypropylene fibers making up the web are preferably of at least two different deniers, such as 3 and 5 denier fibers. The nonwoven webs have a basis weight from about 20 to about 200 grams per square meter, preferably from about 30 to about 100 grams per square meter.

Raw materials, such as individual fibers, that are used in the manufacture of the liquid permeable structure 20, or alternatively the structure's first and second surface 21 and 22 respectively, may optionally be treated with a surface active agent to render the structure more hydrophilic or hydrophobic. To help draw any captured fluid away from a user's body, that is from the first surface 21, the second surface 22 for example may be treated to render it more hydrophilic. In contrast, the second surface 22 may be treated with various fluid repellants to render it significantly hydrophobic to help prevent any captured fluid from transferring to the user's undergarments or other unwanted surfaces.

The barrier layer 30 can be of any flexible material that prevents and/or retards the through transfer of liquid but does not necessarily prevent the passage of gases. Commonly used materials are polyethylene or polypropylene films. The barrier layer may also be an extruded thermoplastic coating, that is directly extruded onto at least portions of the second surface 22, such as disclosed in Sonoda, U.S. Pat. No. 5,089,075. Adhesive coatings, for positioning article 10 in a user's undergarments, may also serve as the barrier layer 30, as described in greater detail below.

Other materials that may be used as the barrier layer are made from those selected from films of polyesters, polyamides, ethylene vinyl acetate, polyvinyl chloride, polyvinylidene chloride, cellophane, nitrocellulose and cellulose acetate. Co-extruded and laminated combinations of the foregoing, wherein such combinations are permitted by the chemical and physical properties of the film, may be used. Liquid impermeable reticulated foams and repellent treated papers may also be used.

Barrier layers that block or retard liquid permeation, but permit gases to transpire, i.e., "breathable barriers", may be used. Single or multiple layers of microporous films, fabrics and combinations thereof, that provide a tortuous path, and/or whose surface characteristics provide a liquid repellent surface to the penetration of liquids may be used to provide such breathable barriers. A nonwoven web particularly useful as a breathable, barrier layer is a spunbond polypropylene web, providing a retarding effect, but not necessarily an absolute barrier, to liquid strikethrough.

Attachment means may occupy portions of the first surface 21 and/or the outwardly disposed surface of the barrier layer 30. Body-adhesives, such as those disclosed in Sieverding, U.S. Pat. No. 4,883,193, may be applied to the first surface 21 for attaching the liquid permeable structure 20 directly to a user's body. Alternatively, positioning adhesives, mechanical fasteners, or high coefficient of friction materials may be applied to the barrier layer 30 for releasably adhering the liquid permeable structure 20 to a user's undergarments or hosiery. Alternatively, the barrier layer itself may be constructed from a high coefficient of friction material, such as natural or synthetic rubber, thereby eliminating the need for additional material to provide undergarment attachment. Useful mechanical fasteners and high coefficient of friction materials are disclosed in the following U.S. Pat. Nos. 4,946,527; 5,058,247; 4,166,464; and 5,011,480.

Preferably, positioning adhesives are used to adhere the article 10 to a user's undergarments. Positioning adhesives suitable for the articles of the present invention are well known in the art, one known class being styrenic block copolymers. Techniques used for applying the adhesives to the article include, but are not limited to slot coating, spraying, knife coating, extrusion coating, and transfer coating. The adhesives may also be foamed prior to application, such as by using commercially available equipment from the Nordson Corporation. Adhesives may be coated in continuous or in discrete patterns from emulsion or solution directly onto the product substrate or onto a release substrate to be subsequently transferred onto the article.

Positioning adhesives may serve as a barrier or repellant to liquid permeation. Puletti et al., U.S. Pat. No. 4,692,161, discloses a hot melt adhesive waste barrier. Embodiments of '161 include coating portions, or all of a nonwoven web with pressure sensitive formulations, so as to form a barrier to replace conventionally employed impermeable films and separate attachment means.

Figure 2:
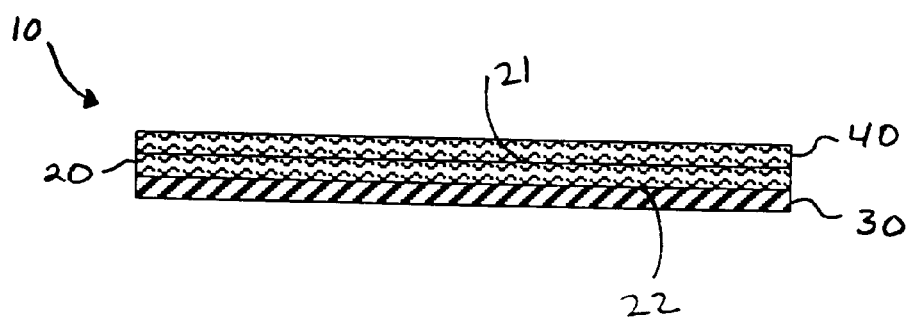
FIG. 2 is an end view of the fluid management article of FIG. 1 depicting an optional cover overlaying a body-facing side of the structure.

As shown in FIG. 2, fluid management article 10 may optionally employ a liquid permeable cover 40, overlaying the first surface 21. The cover 40 is preferably compliant, soft feeling, and non-irritating to a user's skin. The cover should further exhibit good strikethrough and a reduced tendency to rewet, permitting bodily discharges to rapidly penetrate it and flow toward subsequent underlying layers, while not allowing such discharges to flow back through the cover to the skin of the user.

A suitable cover 40 may be manufactured from a wide range of materials including, but not limited to woven and nonwoven fabrics, apertured formed polymeric films, hydroformed films, porous foams, reticulated foams, reticulated thermoplastic films, and thermoplastic scrims. In addition, the cover may be constructed from a combination of one or more of the above materials, such as a composite layer of nonwoven and apertured formed thermoplastic film. Apertured films are well suited for the cover 40 because they are pervious to liquids and, if properly apertured (including tapering), have a reduced tendency to allow liquids to pass back through and rewet the user's skin. Useful films are disclosed in the following U.S. Pat. Nos. 3,929,135; 4,324,426; 4,342,314; 4,463,045; and 5,006,394.

Particularly suitable covers 40 include 30 and 34 grams per square meter versions of a thermobonded multidenier (3 and 5 denier) polypropylene nonwoven web, and 14 and 18 grams per square meter versions of a through-air nonwoven comprising polyethylene sheath and polypropylene core bi-component fibers.

The liquid permeable cover 40 may employ body adhesives on its outwardly disposed surface for attaching the article 10 directly to a user's body. The article can be attached to pubic hair covered parts of the perineum, such as the mons pubis and the vulva. Alternatively, the article can be attached to relatively hairless parts, such as the inner surfaces of the labia majora, the labia minora, and the inward surfaces of the thighs and the cleft between the thighs and the perineum. Multiple areas of body attachment are also provided by the present invention.

FIGS. 1 and 2 and their corresponding description, illustrate preferred embodiments of a first approach to managing low volumes of bodily fluids while maintaining user comfort, wherein the fluid management article 10 contains zero absorbent material. The first approach or substantial equivalents thereto, provide a comfort improvement over the existing art by minimizing the potential for fluid retention at or near the skin-contacting surface. Captured fluid will tend to permeate the interstitial spaces (pores) and settle distal the skin-contacting surface.

Figure 3:
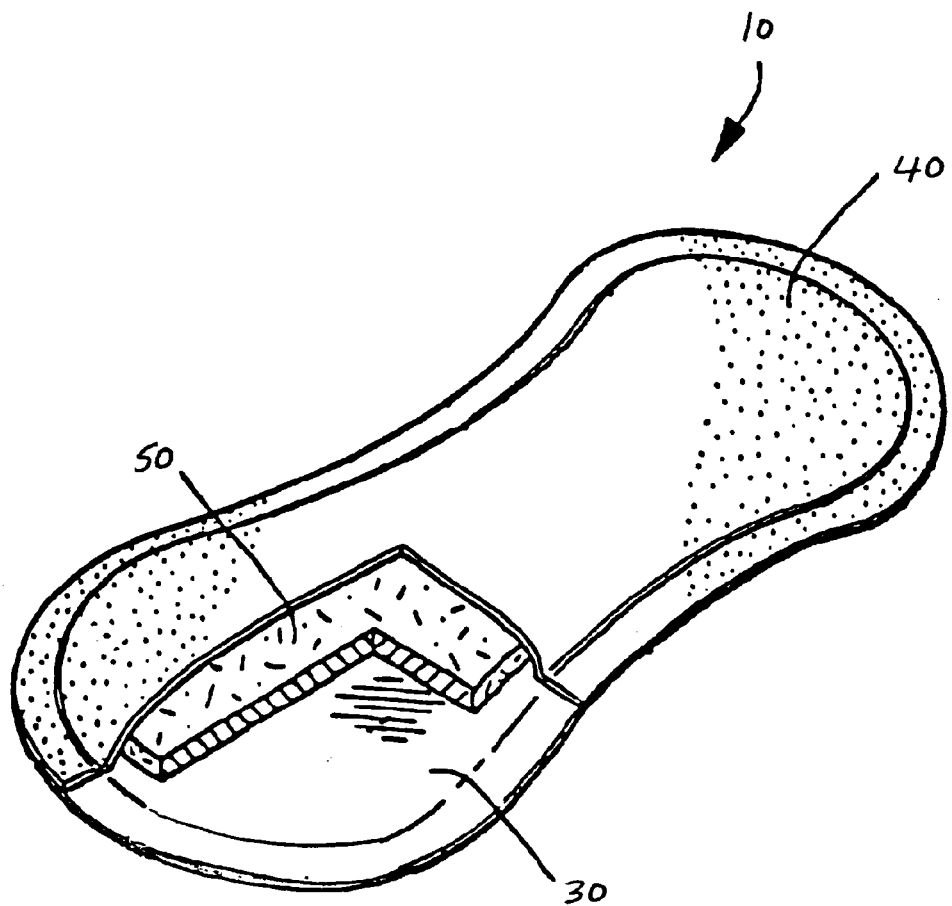
FIG. 3 is a cutaway perspective view of a fluid management article provided by the present invention having a liquid permeable cover, a barrier layer, and an absorbent core intermediate the cover and barrier.

A second approach to managing low volumes of fluid, while maintaining user comfort, employs limited amounts of absorbent material in a core layer, which is buffered from skin contact by a liquid permeable cover. FIG. 3 depicts preferred embodiments relating to the second approach. Fluid management article 10 comprises a liquid permeable cover 40, a barrier layer 30, and an absorbent core 50 intermediate the cover and barrier. The liquid permeable cover 40 and the barrier layer 30 are shown to extend beyond the absorbent core 50. The absorbent core may alternatively, be coterminous with the cover and barrier. Preferably, the absorbent core 50 contains absorbent material in an amount of 0.70 grams or less.

A representative, non-limiting list, of absorbent material useful in the absorbent core 50 includes natural cellulosics, such as cotton and wood pulp; regenerated cellulosics, such as rayon and cellulose acetate; peat moss; hydrogel-forming polymers in the form of fibers or particles, commonly referred to as "superabsorbents"; and the like. One of ordinary skill in the art would readily appreciate that a blend of two or more types of absorbent materials may be used to optimize the performance of fluid management articles used in varying conditions. The absorbent material may be uniformly dispersed within the core 50, or may alternatively be placed in discrete patterns, or in gradients. For example, in an effort to help reduce side leakage, absorbent material may be placed in high concentrations around peripheral portions of the core.

The absorbent core 50 may have a blend of absorbent materials and thermoplastic fibers, for example to provide structural integrity to the formed structure or for heat sealability to additional layers, such as a barrier layer film. Useful thermoplastic fibers are polyolefins, such as polypropylene and polyethylene fibers. The thermoplastic fibers may be bi-component or multi-component fibers having a first component having a first melting temperature and two or more additional components having different melting temperatures to that of the first melting temperature. Bi-component fibers are typically configured sheath-core or side-by-side. Suitable bi-component fibers include polyester/polyethylene and polypropylene/polyethylene A Preferred absorbent core 50 comprises a composite of cellulosic fibers and thermoplastic binder fibers, having a basis weight in the range from about 50 to about 200 grams per square meter. When the absorbent core 50 comprises hydrogel-forming polymers (superabsorbents) as the absorbent material, they will preferably be in quantities significantly less than 0.70 grams, on the order of 0.3 grams or less such that the article does not offer excess absorbent capacity. Absorbent capacities are discussed in more detail below.

Similar to the embodiments described in conjunction with FIGS. 1 and 2, embodiments corresponding to FIG. 3 may contain attachments means on the outwardly disposed surfaces of the barrier layer 30 and/or the cover 40.

The individual layers of the present invention may employ any known assembly techniques for adhering adjacent layers together. A representative, non-limiting list of assembly techniques and materials, includes adhesives, heat seal, ultrasonic welding, solvent welding, and mechanical fastening. Preferably, construction adhesives are used to laminate individual elements to one another. Suitable construction adhesives are disclosed in the following U.S. Pat. Nos. 4,526,577; 5,149,741; and 5,057,571. The construction adhesives may be modified to be absorbing by incorporating absorbing polymer into their formulations.

The fluid management articles of the present invention are intended to manage low volumes of fluid encountered both menstrually, and intermenstrually. Preferably, the various embodiments of the present invention have a total capacity of 1.2 grams or less, as determined by the total capacity test defined in the test methods section.

In addition to fluid capacity, the articles of the present invention are designed to be extremely comfortable and non-obtrusive to a user. The collective design attributes are intended to provide daily confidence without compromise to lifestyle, including activity and clothing. Two variables, which may affect the before mentioned design characteristics, are article caliper and flexibility. Preferably the articles have a caliper of 3.0 millimeters or less, more preferably 2.0 millimeters or less, and most preferably 1.1 millimeters or less. Flexibility is measured by a flexural resistance test, described in great detail in the test methods section. Preferably, the articles have a flexural resistance of 120 grams or less.

The articles of the present invention are also useful for delivering a multitude of additives. A representative, non-limiting list of potential additives includes medicaments, moisturizers, vitamins and minerals, spermicides, and odor controlling agents.

The articles may be of any shape suitable for placement against a user's perineum and the surrounding areas. Shapes include rectangular, oval, dogbone, peanut shape, and the like.

In addition to the elements specifically disclosed in the instant specification, other performance enhancers known in the art may be employed, such as lateral extensions for wrapping around a crotch portion of user's undergarments.

To help prevent fluid leakage from the peripheral portions of the articles, the individual elements themselves, or the finished article, may employ embossments in the form of discrete densified areas or channels.

The articles of the present invention may be individually wrapped in a flat, folded, or rolled configuration for easy portability. The individual wrappings may employ features that render the wrapper useful as a disposal means for soiled articles.

The preparation and properties of fluid management articles according to the present invention are further illustrated by the following examples. The examples are given for the purposes of illustration only and the invention is not limited thereto.

Example A: fluid management articles were constructed comprising a 18 gsm nonwoven cover consisting of polypropylene/polyethylene bi-component fibers, a 65 gsm absorbent core consisting of airlaid pulp and an acrylic binder, and a 24.5 gsm polyethylene film barrier. Fuller HL-1491XZP hot melt construction adhesive was used to adhere adjacent elements. Fuller 1417 positioning adhesive was placed onto the garment-facing surface of the film barrier. The pulp was the only absorbent material present in the articles, at a level of 0.40 grams. The articles had an average caliper of 0.96 millimeters, flexural resistance of 34.23 grams, and total capacity of 1.34 grams.

Example B: fluid management articles may be prepared as follows. Provide a 34 gsm nonwoven web as a liquid permeable structure, wherein the web comprises 3 and 5 denier polypropylene fibers. Provide a 0.8 mil polyethylene film as a barrier layer. Adhere the liquid permeable structure to the barrier layer with a styrenic block copolymer adhesive formulation. The article is void of any absorbent material.

Example C: fluid management articles may be prepared as follows. Provide a 34 gsm nonwoven web as a liquid permeable cover, wherein the web comprises 3 and 5 denier polypropylene fibers. Provide a 0.8 mil polyethylene film as a barrier layer. Provide a 50 gsm nonwoven web as a liquid permeable structure, wherein the web comprises 12 denier polyester fibers. Place the liquid permeable structure intermediate the cover and barrier and adhere the elements with a styrenic block copolymer adhesive formulation. The article is void of any absorbent material.

Test Methods

The total capacity of a fluid management article is determined as follows. Any individual wrapping materials and adhesive release paper is removed from the article to be tested. The article is first weighed to the nearest 0.1 gram. The article is then submerged in a container of 1% saline solution, such that the article is totally submerged and is not bent or otherwise twisted or folded. The article remains submerged for 10 minutes. It is then removed from the saline and suspended for two minutes in a vertical position to allow the saline to drain out of the article. The article is then placed body—facing surface down onto an absorbent blotter, such as Whatmann grade # 1 filter paper available from VWR Scientific of Bridgeport, N.J. A uniform 17.6 grams per square centimeter load is placed over the article to squeeze excess saline out. The absorbent blotter material is replaced every 30 seconds until the amount of saline transferred to the absorbent blotter is less than 0.5 grams in a 30-second period. Next, the article is weighed to the nearest 0.1 gram and the initial weight of the article is subtracted. The difference in grams is the total capacity of the article.

The flexural resistance of the article is measured by peak bending stiffness. Peak bending stiffness is determined by a test that is modeled after the ASTM D 4032.82 CIRCULAR BEND PROCEDURE, the procedure being considerably modified and performed as follows. The CIRCULAR BEND PROCEDURE is a simultaneous multi-directional deformation of a material in which one outwardly disposed surface of the article becomes concave and the opposing surface becomes convex. The CIRCULAR BEND PROCEDURE yields a force value related to flexural resistance, simultaneously averaging stiffness in all directions.

The apparatus required for measuring flexural resistance is a modified Circular Bend Stiffness Tester, having the following parts: A smooth-polished steel plate platform that measures 102.0×102.0×6.35 millimeters, having an 18.75 millimeter diameter orifice. The lap edge of the orifice should be at a 45 degree angle to a depth of 4.75 millimeters. A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter. The plunger is mounted concentric with the orifice, having equal clearance on all sides. A force-measurement gauge and more specifically an Instron inverted compression load cell. The load cell has a load range of from about 0.0 to about 2,000.0 grams. An actuator, and more specifically the Instron Model No. 1122 having an inverted compression load cell. The Instron instrument is made by the Instron Engineering Corporation, Canton, Mass.

Specimens are cut from the articles to be tested, measuring 37.5×37.5 millimeters. The specimens should be cut inward from the periphery in order to ensure that all of the elements of the article are maintained within the specimens. Any individual wrapping and release paper is removed before testing. Any undergarment or body adhesive should be blocked, such as by applying powder to the adhesive, in an effort to prevent the specimens from adhering to the platform, resulting in an artificially high test value. The plate is leveled and the plunger speed is set at 50.0 centimeters per minute per full stroke length. A specimen is centered on the orifice below the plunger such that the body-facing surface is facing the platform. The plunger is then actuated and the maximum force reading to the nearest gram is recorded. Preferably, multiple specimens are cut from a single article and measured, with the average maximum force readings representing the flexural resistance of the article.

The caliper of the article is measured through the use of a comparator gauge, such as those available from the B.C. Ames, Company of Waltham, Mass. The comparator gauge should have a 28.6 millimeters (1⅛ in.) diameter comparator foot. The comparator gauge is zeroed. A 56.7 grams (2 oz.) weight is placed on the spindle extending above the comparator dial. The comparator foot is raised and the article, with any individual wrapping and release paper removed, is placed garment-facing surface down on the base plate. The article is positioned on the base plate so that when the foot is lowered it is in the center of the article. The foot is gently lowered onto the article. The article caliper is determined by reading the comparator dial after the foot comes into contact with the article and the output value is stable (if using digital model is used). The measurement is repeated at each of the ends of the article along its longitudinal centerline. The average of the measurements is the caliper of the article.

The disclosures of all patents, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A fluid management article designed and configured to be worn adjacent a user's perineum, comprising a liquid permeable cover; a barrier layer; and an absorbent core immediate the cover and the barrier layer; the article having a total fluid capacity of 1.2 grams or less.

2. The article of claim 1 having a total capacity of 1.0 grams or less.

3. The article of claim 1 having a caliper of 3.0 millimeters or less.

4. The article of claim 3 having a caliper of 1.1 millimeters or less.

5. The article of claim 1 having a flexural resistance of 120 grams or less.

6. The article of claim 1 wherein the absorbent core comprises 0.7 grams or less of absorbent material.

7. The article of claim 6 which is substantially free of hydrogel-forming polymers.

8. The article of claim 6 wherein the absorbent material comprises cellulosic fibers.

9. The article of claim 8 wherein the cellulosic fiber is wood pulp.

10. The article of claim 1 wherein the liquid permeable cover is a nonwoven web comprising polyolefin fibers.

11. The article of claim 10 wherein the polyolefin fibers are polypropylene fibers of at least two different deniers.

12. A fluid management article designed and configured to be worn adjacent a user's perineum, comprising an absorbent-free, liquid permeable structure having a first surface and a second surface opposite thereof, and; a barrier layer covering at least a portion of the second portion the second surface, the article having a total fluid capacity of 1.2 grams or less.

13. The article of claim 12 further comprising a liquid permeable cover overlaying the first surface.

14. The article of claim 12 having a caliper of 3.0 millimeters or less.

15. The article of claim 14 having a caliper of 1.1 millimeters or less.

16. The article of claim 12 wherein the liquid permeable structure is an apertured film.

17. The article of claim 16 wherein the apertured film is an apertured formed film.

18. The article of claim 17 wherein the apertures have tapered capillaries.

19. The article of claim 12 wherein the liquid permeable structure is a nonwoven web.

20. The article of claim 19 wherein the nonwoven web comprises polyester fibers.

21. The article of claim 19 wherein the nonwoven web comprises polyolefin fibers.

22. The article of claim 12 wherein the first surface is hydrophobic and the second surface is hydrophilic.

23. A fluid management article designed and configured to be worn adjacent a user's perineum, comprising a liquid permeable cover; a barrier layer; and an absorbent core intermediate the cover and the barrier; the absorbent core being substantially free of hydrogel-forming polymers and comprising 0.7 grams or less of absorbent material.

24. The article of claim 23 comprising 0.3 grams or less of absorbent material.

\* \* \* \* \*